(12) United States Patent
Weston et al.

(10) Patent No.: US 9,555,401 B2
(45) Date of Patent: *Jan. 31, 2017

(54) MOLECULAR SIEVE ADSORBENT BLENDS AND USES THEREOF

(71) Applicant: ZEOCHEM LLC, Louisville, KY (US)

(72) Inventors: Kerry Weston, Louisville, KY (US); Patrick Purcell, Louisville, KY (US)

(73) Assignee: ZEOCHEM LLC, Louisville, KY (US)

( * ) Notice: Subject to any disclaimer, the term of this patent is extended or adjusted under 35 U.S.C. 154(b) by 362 days.

This patent is subject to a terminal disclaimer.

(21) Appl. No.: 14/222,896

(22) Filed: Mar. 24, 2014

(65) Prior Publication Data

US 2014/0217324 A1    Aug. 7, 2014

Related U.S. Application Data (60) Division of application No. 14/222,870, filed on Mar. 24, 2014, now Pat. No. 8,969,633, and a continuation-in-part of application No. 13/013,285, filed on Jan. 25, 2011, now Pat. No. 8,680,344, and a continuation-in-part of application No. 13/923,096, filed on Jun. 20, 2013, now Pat. No. 9,050,582.

(51) Int. Cl.

| | |
|---|---|
| *B01J 29/06* | (2006.01) |
| *B01J 20/18* | (2006.01) |
| *B01J 29/70* | (2006.01) |
| *C07C 7/13* | (2006.01) |
| *C07C 29/76* | (2006.01) |
| *C10G 25/03* | (2006.01) |
| *C10G 11/00* | (2006.01) |
| *C10G 33/04* | (2006.01) |
| *B01J 37/00* | (2006.01) |

(52) U.S. Cl.
CPC ............ *B01J 29/7003* (2013.01); *B01J 20/18* (2013.01); *B01J 20/183* (2013.01); *C07C 7/13* (2013.01); *C07C 29/76* (2013.01); *C10G 11/00* (2013.01); *C10G 25/03* (2013.01); *C10G 33/04* (2013.01); *B01J 37/0009* (2013.01); *B01J 37/0063* (2013.01); *B01J 2229/42* (2013.01)

(58) Field of Classification Search
USPC ....................................... 502/63, 64, 68, 407
See application file for complete search history.

(56) References Cited

U.S. PATENT DOCUMENTS

| | | | |
|---|---|---|---|
| 2012/0118160 A1 | 5/2012 | Heffes et al. | |
| 2013/0340615 A1* | 12/2013 | Barrett | B01J 20/183 |
| | | | 95/96 |

FOREIGN PATENT DOCUMENTS

| | | |
|---|---|---|
| EP | 0940174 | 9/1999 |
| GB | 827043 | 2/1960 |
| WO | WO 2012/103055 | * 8/2012 |

OTHER PUBLICATIONS

International Search Report and accompanying Written Opinion, dated Oct. 14, 2014, with respect to International Application No. PCT/US2014/043107.

* cited by examiner

*Primary Examiner* — Elizabeth Wood
(74) *Attorney, Agent, or Firm* — Scott R. Cox (57) ABSTRACT

A molecular sieve blend with improved performance characteristics produced by preparing or obtaining a hydrophilic zeolite, particularly a hydrophilic zeolite A with a low $SiO_2:Al_2O_3$ ratio, preparing or obtaining a hydrophobic silicon based binder, particularly a hydrophobic colloidal silica or a hydrophobic siloxane based material, mixing the zeolite with the silicon based binder and, in one embodiment, a seed containing small quantities of a clay binding agent and the zeolite, to form a mixture, and forming the mixture into the molecular sieve blend.

20 Claims, 7 Drawing Sheets

MOLECULAR SIEVE ADSORBENT BLENDS AND USES THEREOF

CROSS REFERENCE TO RELATED APPLICATIONS

This is a divisional application of U.S. patent application Ser. No. 14/222,870, filed Mar. 24, 2014, now U.S. Pat. No. 8,969,633, and is also a continuation-in-part application that claims the benefit of U.S. patent application Ser. No. 13/013,285, filed Jan. 25, 2011, now U.S. Pat. No. 8,680,344, and is also a continuation-in-part application that claims the benefit of U.S. patent application Ser. No. 13/923,096, filed Jun. 20, 2013, now U.S. Pat. No. 9,050,582, the disclosures of which are incorporated by reference herein.

BACKGROUND

Various embodiments relate to molecular sieve blends containing a combination of a hydrophilic zeolite, and a hydrophobic silicon based binder and preferably, a seed, preferably formed in a granulation process, utilized in the preparation of the molecular sieve blends, wherein the seed, in one embodiment, contains a clay binding agent, and processes of manufacture and use of these molecular sieve blends, such as for dehydration of liquid and gaseous hydrocarbon streams, drying of cracked $C_1$-$C_4$ hydrocarbon gas streams, dehydration of ethanol feed streams, and removal of various undesired materials from various types of feed streams. (For purpose of this disclosure "molecular sieve blends" are alternatively referred to as "adsorbents", "adsorbent blends", "molecular sieve adsorbent blends" or "molecular sieve adsorbents" or similar terms.)

Zeolites are hydrated metal alumino silicates having the general formula $$M_{2/n}O:Al_2O_3:xSiO_2:yH_2O$$

where M usually represents a metal of an alkali or alkaline earth group, n is the valence of the metal M, x varies from 2 to infinity, depending on the zeolite structural type and y designates the hydrated status of the zeolite. Most zeolites are three-dimensional crystals with a crystal size in the range of 0.1 to 30 µm. Heating these zeolites to high temperatures results in the loss of the water of hydration, leaving a crystalline structure with channels of molecular dimensions, offering a high surface area for the adsorption of inorganic or organic molecules. Adsorption of these molecules is dependent upon the size of the zeolite channels. The rate of adsorption is limited by the laws of diffusion.

Zeolites are used for a number of processes. The choice of zeolite is important in a number of chemical processes well known to those skilled in the art. For example, catalytic processes of interest using zeolites in the petrochemical industry include reforming, hydrocracking, dewaxing, isomerization, fluid catalitic cracking (FCC), partial oxidation, alkylation and disproportionation of aromatics. Zeolites are also used for dehydration, adsorption of various compounds from feed streams and separation of various hydrocarbons in a feed stream.

Molecular sieves have been advantageous for a number of processes as the diffusion of materials into and out of the pores can be facilitated based on the pore size that is present within the particular molecular sieve. (For purposes of this disclosure "zeolite" and "molecular sieve" have the same meaning.)

One limitation on the utilization of zeolites is their extremely fine particle size. Large, naturally-formed agglomerates of zeolite crystals break apart easily. In addition, because the pressure drop through a bed containing only such fine zeolite crystals is prohibitively high, these zeolite crystals cannot be used alone in fixed beds for various dynamic applications, such as drying of natural gas, drying of air, separation of impurities from a gas stream, separation of some gaseous and liquid product streams and the like. Therefore, it is necessary to agglomerate these zeolite crystals with binder materials to provide an agglomerate mass containing the zeolite crystals, which exhibits a reduced pressure drop.

To overcome these issues and permit the utilization of zeolite crystals, different types of clays have conventionally been used as binder materials for those crystals, wherein the clay binders have generally been selected from attapulgite, palygorskite, kaolin, sepiolite, bentonite, montmorillonite, other types of clays and mixtures thereof. Particularly useful clay binders are formed from attapulgites.

In one example of the utilization of a molecular sieve adsorbent, water is removed from a cracked gas stream, for example, for the production of ethylene. The molecular sieve adsorbent is utilized immediately before a cryogenic process to remove water so that ice is not created during the process. However, inherent in the process is the fact that the hydrocarbon feed stream contains unsaturated hydrocarbons, such as alkenes and dienes, which are very reactive. These unsaturated hydrocarbons tend to form oligomers and polymers, which act as bed fouling agents and are commonly referred to as green oil or coke. These agents block adsorption channels, reduce the working capacity of the bed for dehydration and reduce useful adsorption life of the adsorbent. Accordingly, it is also important that the molecular sieve adsorbents produce very low quantities of green oil or coke during an adsorption process. Many of the clay binders that have been traditionally used as binder materials with zeolites contain metallic acid sites that encourage polymer/oligomer formation by a catalytic reaction. Conventionally, these clay binder materials are treated with a de-activating agent such as a phosphate solution to reduce this catalytic activity. Notwithstanding, there are still issues associated with the production of green oil/coke during processes for treatment of hydrocarbon feed streams when clay materials are used as the binder material with zeolites.

Silicon based materials have sometimes been used as a binder material with high silica molecular sieves to form catalyst agglomerates for specialty catalytic reactions, wherein the molecular sieves used have included, for example, ZSM-5, Y zeolites and SAPO zeolites. Because of the hydrophobic nature of both the silicon based binders and the high silica zeolites, these catalytic materials have been limited in use to organic reactions. For example, hydrophobic silicon based binders blended with hydrophobic high silica zeolites have been utilized as catalytic materials in the petrochemical industry for reactions including reforming, hydrocracking, dewaxing, isomerization, partial oxidation, alkylation, disproportionation of aromatics, and particularly as fluid catalytic cracking catalysts. These catalytic reactions conventionally utilize hydrophobic zeolites having a high silica content, wherein the $SiO_2$:$Al_2O_3$ ratio is at least 50, preferably greater than 200 and as high as 600 or so. To enhance the high silica content of these zeolites, they are often dealuminized to increase their silica:alumina ratio, making them even more hydrophobic. The silicon based binders used with these catalysts are also required to be highly hydrophobic. Binders used to produce catalysts for these catalytic reactions are not included within this disclosure. Further, the binders of this disclosure are not conventionally utilized to form these catalysts.

One problem with many conventionally formed zeolite agglomerate blends is decreased diffusion. The larger the diameter of the formed zeolites, the slower the rate of diffusion of the molecules to be adsorbed. Particularly in the field of pressure swing adsorption, this effect is highly adverse to short cycle time and thus to productivity. Enhanced kinetic values or faster mass transfer rates can result in shorter cycle time and lower power consumption and thus higher adsorbent productivity.

Another important issue in choosing an appropriate adsorbent is the ability of that adsorbent to selectively adsorb a compound that is desired to be removed from the processing stream without also adsorbing the desired component or components of that stream. For example, an important feature of adsorbents used to remove water from an ethanol feed stream is not only their water adsorption capacity but also that the quantity of ethanol that is adsorbed by the adsorbents is limited. Frequently, it is necessary to balance the relative adsorption capabilities of these adsorbents.

Accordingly, it is one intent to disclose a process for the production of molecular sieve blends which are effective and highly selective for the removal of water from hydrocarbon feed streams, such as those containing ethanol or cracked gases.

It is a still further intent to disclose molecular sieve blends which maintain their physical properties and diffusion capabilities even with a reduced quantity of binder than is conventionally used.

It is a still further intent to disclose molecular sieve blends which limit the production of undesired oligomers and polymers during utilization.

It is an additional intent to disclose a process for the preparation of molecular sieve blends with enhanced diffusion rates.

It is a still further intent to disclose a process for the production of molecular sieve blends containing a hydrophobic silicon based binder that are effective and selective for adsorption processes.

It is a still further intent to disclose molecular sieve blends comprising a low silica, hydrophilic zeolite blended with a hydrophobic silicon based binder.

It is a still further intent to disclose molecular sieve blends comprising a low silica, hydrophilic zeolite, a hydrophobic silicon based binder and a seed comprising, in one embodiment, a clay binding agent, wherein a granulation seed process is utilized to produce the seeds used for the production of the molecular sieve blends.

It is a still further intent to disclose molecular sieve blends comprising a low silica, hydrophilic zeolite blended with a hydrophobic silicon based binder, and a seed, preferably comprising a clay binding agent, wherein a granulation seed process is utilized for the production of the seed, and wherein the seeds utilized in the granulation seed process comprises less than 25% by volume of the molecular sieve blends.

It is still further intent to disclose molecular sieve blends comprising a low silica, hydrophilic zeolite blended with a hydrophobic silicon based binder and a seed, preferably comprising a clay binding agent, wherein a granulation seed process is utilized for the production of the seed, wherein the composition of the seeds comprises clay and the hydrophilic zeolite, and wherein the clay comprises less than 5% by weight of the overall molecular sieve blends.

It is a still further intent to disclose a process for drying a feed stream comprising passing the feed stream over molecular sieve adsorbent blends comprising a low silica, hydrophilic zeolite, a hydrophobic silicon based binder, and a seed used for the production of the molecular sieve blends, preferably comprising a clay binding agent and the hydrophilic zeolite.

It is a still further intent to disclose a process for the separation of polar materials using molecular sieve blends comprising a zeolite, particularly a low silica hydrophilic zeolite, more particularly a low silica hydrophilic zeolite 3A, a hydrophobic silicon based binder, particularly a hydrophobic colloidal silica binder or, in a less preferred embodiment, a hydrophobic siloxane based binder, and a seed used in the production of the molecular sieve blends, preferably comprising a clay binding agent and the hydrophilic zeolite.

It is still further intent to disclose a process for separation of components of a gaseous or liquid feed stream, particularly an ethanol feed stream, comprising passing that gaseous or liquid feed stream over molecular sieve blends comprising a low silica hydrophilic 3A zeolite powder, a hydrophobic colloidal silica binder or, in a less preferred embodiment, a hydrophobic siloxane based binder, and a seed used in the production of the molecular sieve blends, preferably comprising a clay binding agent and the hydrophilic zeolite.

These and other intents are obtained from the processes for production, the processes for use and the products of the various embodiments disclosed herein.

SUMMARY OF THE EMBODIMENTS

One embodiment is molecular sieve blends comprising a hydrophilic zeolite, particularly a low silica hydrophilic zeolite 3A, blended with a hydrophobic silicon based binder, particularly a hydrophobic colloidal silica binder or, in a less preferred embodiment, a hydrophobic siloxane binder and processes for the production of these blends.

An additional embodiment is molecular sieve blends comprising a hydrophilic zeolite, particularly a low silica hydrophilic zeolite 3A, blended with a hydrophobic silicon based binder, and a seed, wherein a granulation seed process is utilized for the production of the seed, wherein the seeds preferably comprise a clay binding agent and the hydrophilic zeolite, and wherein the clay binding agent comprises less than 5% by weight of the molecular sieve blends and processes for the production of these blends.

An additional embodiment is a process for drying a gaseous or liquid hydrocarbon feed stream, such as an ethanol feed stream, comprising passing the feed stream over or through molecular sieve blends comprising a zeolite, particularly a low silica, hydrophilic zeolite 3A, blended with a hydrophobic silicon based binder, particularly a hydrophobic colloidal silica binder or, in a less preferred embodiment, a hydrophobic siloxane based binder which are selective.

An additional embodiment is a process for the separation of components of a hydrocarbon gaseous or liquid feed stream comprising passing the feed stream over or through molecular sieve blends comprising a zeolite, particularly a low silica, hydrophilic zeolite, blended with a hydrophobic silicon based binder, particularly a hydrophobic colloidal silica binder or, in a less preferred embodiment, a hydrophobic siloxane based binder.

Additional embodiments include processes for drying a gaseous or liquid hydrocarbon feed stream, such as an ethanol feed stream, or separation of components of a hydrocarbon gaseous or liquid feed stream, comprising passing the selected feed stream over or through molecular sieve blends comprising a zeolite, particularly a low silica, hydrophilic zeolite, blended with a hydrophobic silicon based binder, particularly a hydrophobic colloidal silica binder or, in a less preferred embodiment, a hydrophobic siloxane based binder, and a seed, preferably comprising a clay binding agent and the hydrophilic zeolite, wherein a granulation seed process is utilized for the production of the seed, and wherein the clay comprises less than 5% by weight of the blends.

Among those benefits and improvements that have been disclosed, other objects and advantages will become apparent from the following description taken in conjunction with the accompanying drawings. The drawings constitute a part of the specification and include exemplary embodiments and illustrate various objects and features thereof.

DETAILED DESCRIPTION OF ONE EMBODIMENT

One embodiment is molecular sieve blends formed from a hydrophilic zeolite blended with a hydrophobic silicon based binder and processes for formation and use of those blends and processes for the production of these blends.

These embodiments are based on the surprising discovery that the adsorption rate and selectivity of a molecular sieve products are dependent not only upon the choice of the zeolite, but also the type and characteristics of the binder blended with the zeolite to form the molecular sieve blends. It has been surprisingly discovered that the same type of zeolite, when blended with different types of binders, produces zeolite blends which exhibit entirely different performance characteristics, depending upon the binder that is used. (For purposes of this disclosure, the phrases "adsorption rate" or "absorption rate" or "sorption rate" or "mass transfer rate" mean the rate at which the adsorbate loading in a feed stream changes over a given period of time for a given adsorption process.)

The prior art suggests that the adsorption rate and selectivity of molecular sieve adsorbents is a function of the porosity and particle size of the molecular sieve only. The prior art also suggests that the adsorption rate and selectivity of a molecular sieve used in a hydrocarbon feed stream is a function of the hydrophobicity of each of the components of the molecular sieve blend. For example, conventional zeolite adsorbent blends used with hydrocarbon feed streams utilize zeolites and binders which are both hydrophobic. Thus, when zeolite blends are conventionally used for non-polar separations, such as removal of volatile organic compounds (VOC's), the zeolite:binder system is conventionally comprised of two components which are both hydrophobic. In contrast, zeolite blends conventionally used for polar separations, such as water removal from methanol or cracked gases, are conventionally comprised of a zeolite:binder system, where both components are hydrophilic.

It has now been surprisingly discovered that the type of binder that is used to bind zeolite crystals plays an important role in the adsorption rate and selectivity of the zeolite blend. It has also been surprisingly discovered that when a polar separation is desired, such as for the adsorption of water from a hydrocarbon feed stream, the use of a hydrophilic zeolite and a hydrophobic silicon based binder is surprisingly effective to remove water and also surprisingly exhibits improved performance over prior art zeolite blends. These improvements include, but are not limited to, a reduction in the production of green oil or coke, enhanced adsorption characteristics and improved selectivity.

The zeolites, as used for preparing the molecular sieve blend according to the present invention, can be in any form. Preferably the zeolites are in the form of crystals, crystal aggregates, or mixtures thereof. It is also possible to use a mixture of different types of zeolites for preparing the molecular sieve blend. Within the context of the present invention, the term "molecular sieve blend" refers to a blend of materials that can be formed into a shaped material suitable for the desired absorption processes. The molecular sieve blends are preferably formed by preparing a mixture comprising one or more types of zeolite, and one or more types of binder material and, in a preferred embodiment, a seed formed in a granulation process. The mixture can then be further processed, e.g. formed into a desired shape and calcined, as described herein.

In one preferred embodiment, the molecular sieve blends are prepared by using a mixture comprising or consisting of one or more types of hydrophilic zeolites, and one or more types of hydrophobic silicon based binders. Various types of zeolites may be used to form these adsorbent blends, depending on the material to be adsorbed and the remaining materials in the feed stream. Alternative compositions of the binder material utilizing a seed granulation process are discussed later.

Different types of zeolites that have been used for adsorption of various materials include, for example, zeolite A, zeolite X, zeolite Y, zeolite ZSM-5, zeolite Beta, synthetic mordenite and blends thereof. The ion-exchange of these zeolites can also vary, but generally utilizes alkali and/or alkaline earth metals. The zeolites, as used for preparing the molecular sieve blends, have a crystal size, preferably in a range from 0.1 to 30 µm.

One example of an adsorbent system using the molecular sieve blends disclosed herein adsorbs water from an ethanol stream. For ethanol dehydration, the co-adsorption of ethanol is a major process inhibitor as ethanol is the bulk component in the process feed mixture. Co-adsorption of ethanol hinders the dehydration process because: 1) water adsorption sites on the zeolite become occupied or blocked with water, and 2) the desired product (ethanol) is lost during the purge cycle, resulting in lower (relative) product recovery. As the process for dehydration of ethanol is a process swing adsorption process, the goal of any product development includes improvement in both the adsorption of the adsorbate (water selectivity) and reduction in the adsorption of the desired product (ethanol).

Another use for the molecular sieve blends disclosed herein is the drying of cracked gases, more particularly the drying of a thermally cracked hydrocarbon gas stream by contacting said stream with zeolite blends. During such process, if water is not removed, hydrocarbon hydrates are formed which deposit as solids which can plug pipe lines, freeze valves and regulators and foul fractionating columns, wherein the cracked gas is demethanized for the recovery of unsaturated hydrocarbons. For example, during the conventional separation of ethylene, the temperature of the feed stream is sufficiently low and the pressure is sufficiently high that any water present in the feed stream often forms hydrates with ethylene. These hydrates accumulate to produce solids which may render the column incapable of passing the required vapor or liquid load. One method of solving this problem has been by use of desiccants. However, desiccants have disadvantages because of their short life. Another method of drying cracked gases is the use of zeolite adsorbents. However, because of the size of zeolite crystals, it is necessary for them to be mixed with a binder material to form agglomerates before use for this process. Problems associated with the use of these binders have been previously discussed.

A particularly effective zeolite that is useful for removal of water from an ethanol:water mixture and for the drying of cracked hydrocarbons is zeolite 3A. Zeolite 3A is particularly effective for the adsorption of water because of the size of the pore openings in this zeolite, which permits the passage of water molecules but restricts the passage of larger hydrocarbon molecules, including ethanol. While zeolite 3A is an especially useful zeolite for this and related processes, other zeolites may also be used for other processes, such as the use of zeolite 5A for iso/normal paraffin separation.

To enhance the water adsorption capability of zeolites, it has been surprisingly discovered that the zeolites, preferably zeolite A, particularly zeolite 3A, should be ion-exchanged with potassium. The extent of ion exchange with potassium ions often depends on the ultimate use for the molecular sieve blends containing zeolites.

In one example, when a zeolite 3A is used for the adsorption of water from an ethanol feed, it is necessary to balance the capacity of the adsorbent to adsorb water against its ability to co-adsorb ethanol from the feed. Industry standards generally suggest that the ethanol adsorption level should be maintained below about 2 mmol/g when measured at 32 mbar and 298° K or so. When balancing the adsorption of water against the adsorption of ethanol, it was surprisingly discovered that it is necessary that the potassium ion exchange of the zeolite 3A should be greater than 30%, preferably greater than 40%, and most preferably greater than 50%. While increases in the potassium ion exchange of the zeolite 3A used in the adsorbents above 65% may further reduce the quantity of ethanol that is co-adsorbed, at this ion exchange level, dramatic decreases in water adsorption capacity of the adsorbents occur.

Additionally, it is necessary to control the extent of ion exchange of the zeolite with potassium ions so that a proper pore closure in the adsorbents is obtained, such that the selectivity for water adsorption can be controlled relative to the polar hydrocarbon species within the feed gas. The pore opening can be controlled by limiting the extent of potassium ion exchange of the zeolite and, in one example, the results can be approximated by the heat of adsorption from exposing adsorbents to a blend of water and liquid methanol.

It is necessary to balance the total water adsorption capacity as well as the pore closure (selectivity) so that the most preferable adsorbents for the desired application is achieved. Thus, it is preferable for commercial processes that the best balance of water adsorption capacity with the adsorption of polar material, such as ethanol, requires an ion exchange with potassium of the zeolite from about 45 to 65%.

The remaining cations of the zeolite can be sodium ions or the zeolite can be exchanged with other alkali or alkaline earth metal ions that do not interfere with the adsorption by the zeolite 3A of water or the passage of the hydrocarbons through the zeolite 3A blends.

In one particular embodiment, the zeolite chosen is a low silica, hydrophilic zeolite with a ratio of $SiO_2:Al_2O_3$ less than 50, alternatively less than 20, alternatively less than 10, alternatively less than 5 and as low as 1. It is useful to reduce the SiO2:Al2O3 ratio of these zeolites to produce zeolites particularly effective for the adsorption of polar substances, particularly water. Processes for the production of low silica zeolites are well known. Low silica zeolites, because they are hydrophilic, as defined in Example 4 hereinafter, are more effective as adsorbents of water from hydrocarbon/water mixtures than are high silica zeolites, which are commonly used, for example, for catalytic reactions. (Zeolite blends useful for such catalytic reactions are not disclosed herein. Further, the zeolite blends of this disclosure are not conventionally utilized for these catalytic reactions.) In addition, such low silica zeolites reduce the likelihood of production of green oil and coke during such processes.

Binder materials are necessary for use with these hydrophilic zeolites to bind the individual zeolite crystals together to form shaped products which reduce the pressure drop during the adsorption process. However, in the past, the binder materials have not enhanced the adsorption capability and selectivity of the zeolite. In fact, prior art binder materials have generally reduced the adsorption capacity of the zeolites and have resulted in the production of undesirable oligomers and polymers (green oil and coke). Binder materials which have been utilized with zeolites in the past generally include clay products, such as kaolin, palygorskite-type minerals, particularly attapulgite, and smectite-type clay minerals, such as montmorillonite or bentonite. These clay products were chosen for various reasons including their hydrophilicity. These clay binders were used singly or in mixtures of two or more different types of clay binders.

These clay binders, particularly attapulgites, often have a high metal content. Such metals can cause carbon polymerization to occur at the acid sites on the clay binder during utilization in the processes disclosed herein. This often results in the production of coke and green oil, resulting in a shortened life span for the zeolite blend. These prior art zeolite/clay binder agglomerate materials, when used for adsorption or separation processes often exhibited a high incidence of coking in the presence of unsaturated hydrocarbons. One advantage of the zeolite blend disclosed herein is a reduction in the polymerization of hydrocarbons and a reduction in the production of coke and green oil and thus, an increase in the life expectancy of the adsorbent.

It has been surprisingly discovered that improved performance from the adsorbent materials can be achieved when the binder material that is used is a silicon based material, especially when the silicon based material is hydrophobic. For purpose of this disclosure, a silicon based material is "hydrophilic" or "hydrophobic" based on the definition contained in Example 4.

In one embodiment, the molecular sieve blend comprises a low silica zeolite with a ratio of $SiO_2:Al_2O_3$, as defined herein, and silicon based material, preferably colloidal silica or, in a less preferred embodiment, a siloxane, wherein the silicon based material preferably has been treated, if necessary, to make at least a portion or substantially all of its surface hydrophobic. The silica can be treated according to methods well known in the art to produce a hydrophobic surface. For example, the treatment can be carried out by treating the silicon based material with a hydrophobizing agent e.g. an agent comprising a hydrolyzable silicon compound having at least one alkoxy group in the molecule or a hydrolyzate thereof.

The hydrophobic silicon based material that is used as the binder, in one embodiment, is a colloidal silica. Colloidal silicas are generally suspensions of amorphous, non-porous and typically spherical silica particles in a liquid phase. One example is Ludox® produced by Grace Davison, wherein the pH of this colloidal silica is about 10. The concentration of silica in the colloidal silica, the silica ratio of $SiO_2:Al_2O_3$, the size of the silica particles and the surface area of the silica particles may vary in the colloidal silica.

In an alternative, less preferred embodiment, the silicon based material is a siloxane based material. Embodiments of siloxane based materials may include, for example, dimethyl siloxane, silsesquioxane or blends thereof or other well-known siloxane based materials. One particular example of a siloxane based material is IE-2404 emulsion from Dow Corning, which contains 40-70% dimethyl siloxane with methyl silsesquioxanes, and x-octyl silsesquioxanes.

Applicants have surprisingly discovered that molecular sieve blends produced using colloidal silica produced better performing adsorbents than traditional adsorbents, wherein the zeolite is bound using a clay binder, such as attapulgite, and also better than adsorbents wherein the binder comprises a siloxane based material. It was surprisingly discovered that molecular sieve blends using colloidal silica materials as binders have better performance for water capacity, water/ethanol adsorption selectivity, breakthrough time, length of unused bed (LUB), and pore distribution coefficient, as later defined. Comparisons of the performance of molecular sieve blends utilizing a colloidal silica binder versus adsorbent materials utilizing conventional attapulgite binders or siloxane based materials are shown in various Examples and Figures.

Once the appropriate zeolite material is chosen for a given application, such as a low silica, hydrophilic zeolite A, preferably a zeolite 3A for water adsorption, it is mixed with a hydrophobic silicon based binder, preferably a colloidal silica, or, in a less preferred embodiment, a siloxane based material, in the presence of water. The hydrophilic zeolite 3A powder and the hydrophobic silicon based binder are then blended together with water. The amount of hydrophobic silicon based binder that is utilized in relation to the hydrophilic zeolite, can range from about 2 to about 30 percent by weight, alternatively from about 2 to about 20 percent and in a further alternative, from about 2 to about 10 percent of the final adsorbent blend.

It has been surprisingly discovered that improved adsorbent blends can be produced when seeds produced by a granulation seed process are utilized in the manufacture of the blends. The composition of the seed produced by this granulation process, in one preferred process, comprises a zeolite, particularly a zeolite 3A, and a clay binder. In addition, depending on the process used for the production of the molecular sieve blends, some silicon based binder can also be included in the seed. However, the quantity of this silicon based binder material that is present in the seed remains relatively low, generally less than 10%, or so.

The use of a clay material in the seed forming process has been determined to be particularly advantageous to increase the manufacturing yield and/or the manufacturing throughput over adsorbent blends prepared without use of a seed. In this process the clay and the zeolite are used to form seeds or nuclei of the adsorbent products to stimulate the agglomeration process. Typically, for this embodiment, the seeds comprise from about 0.5% to about 25% by volume of the agglomerated adsorbent blends. The total amount of the clay that is present in the blends should not exceed about 5%, preferably not more than 3% on a dry weight basis of the components of the adsorption blends. In relation to the silicon based binder, there is preferably less than 1 part clay binder to 5 parts silicon based binder and more preferably less than 1 part clay binder to 20 parts silicon based binder. The minimum amount of the clay binder present in the adsorption blends is about 0.5%, on a dry weight basis.

Many types of clay materials have been utilized as binder materials in prior art adsorption products, including kaolin, palygorskite-type minerals, particularly attapulgite, smectite-type clay minerals, such as montmorillonite or bentonite, halloysite and sepiolite. Any of these clay materials, or other activated clay materials, such as Actigel®, may be utilized as the clay component of the seed.

In an alternative embodiment, instead of the use of clay materials to form the binder for the seed of the adsorbents, use of the silicon based materials earlier described as a binder with the zeolite may also be useful in the formation of the adsorbents. The quantity of the silicon based material that is used to form the seed, as well as the overall volume of the seed made from the silicon based material, is consistent with the quantities of the clay materials that are described herein.

Generally the process to produce the molecular sieve blend with improved adsorption performance characteristics using a seed is as follows: Prepare the seed by combining a zeolite with a clay binder material (and small quantities of a silicon based binder, if desired) at an approximate ratio on a dry weight basis of about 80 to 95% zeolite to 5 to about 20% clay. The formed seed forms the core of the adsorbent blends with the seed particle comprising from about 0.5 to about 25% by volume of the agglomerated particles. Preferably, the amount of the seed particle should be maintained as low as possible while still permitting the desired granulation effect. It has surprisingly been found that agglomerated seed particles made only of the silicon based binder with the zeolite utilized to initiate the agglomeration step are generally not as effective in producing the controlled particle growth that is required for commercial utilization of adsorbents and result in a lower yield, increased manufacturing time, and result in a less efficient production process.

Following the preparation of the seed material containing a clay binder and appropriate quantities of the zeolite, (and small amounts of the silicon based binder, if desired), the mixture of hydrophobic silicon based binder and hydrophilic zeolite is blended with the seed until appropriately sized adsorbent particles are produced. The products can be formed in conventional shapes, such as beads, pellets, tablets or other such products.

An important additional processing step commonly utilized for the production of shaped zeolite based adsorbents is the introduction of a plasticizer, pore former and/or temporary binder, particularly a cellulose containing material, particularly methyl cellulose. Materials such as a polysaccharide, a polyvinyl alcohol starch or other mixtures are sometimes utilized as a substitute for methyl cellulose as a plasticizing agent, as long as they are soluble in water. For example, in U.S. Pat. No. 6,458,187, which describes a shaped body produced from a zeolite and a siloxane-based binder, a required component of the shaped body was methyl cellulose, used as a plasticizer, in quantities from about to about 40%, by weight. In contrast, it has been surprisingly discovered that the addition of methyl cellulose, or similar plasticizing agents, to the adsorbent blends disclosed herein has a detrimental effect on the production of the adsorbent blends and the properties of those produced adsorbent blends. Specifically, it has been surprisingly discovered that the use of methyl cellulose in these adsorbent blends has an adverse effect on the final pore structure of the adsorbents for some applications, resulting in adsorbent blends that are not as useful as those of the preferred embodiments. Further, the use of methyl cellulose has been found to reduce the overall manufacturing yield. Further, the presence of methyl cellulose has been found to produce products with low sphericities and/or shape factors, which are undesirable from the standpoint of increasing the pressure-drop in packed bed adsorption processes, compared to blends formed of equivalent size having high sphericities and shape factors. Accordingly, in a preferred embodiment, cellulose based plasticizers, particularly methyl cellulose, are not utilized in the manufacture of the preferred molecular sieve adsorbent blends. In a more preferred embodiment, it is an important element of the process of manufacture that such plasticizers, including specifically cellulose based plasticizers, such as methyl cellulose, not be used as in the process of manufacture of the adsorbent blends.

It is possible that certain pore forming agents, such as saw dust or other ground organic materials, may be utilized, but are not required elements of the disclosed adsorbents.

Once the formed products are produced into the appropriate shape, they are hydrothermally treated (or calcined) to reduce the pore openings to a size that excludes the desired hydrocarbon, such as ethanol, but retains the capacity to adsorb water from a feed stream. It has surprisingly been discovered that the temperature of calcination of the formed adsorbent blends is important with regard to the properties of the adsorbent blends. In prior art, such as U.S. Pat. No. 6,458,187, it was taught that to maintain the maximum compressive strength of adsorbent products, calcination must occur at temperatures within a narrow temperature range from 180° C. to about 280° C. U.S. Pat. No. 6,458,187 determined that calcination at temperatures above 280° C. resulted in the splitting off of methyl groups from the siloxane binders that were used in their adsorbent products, which weakened their final compressive strength.

In contrast, it has surprisingly been discovered that, in order to produce shaped adsorbent blends exhibiting the adsorption properties necessary for the processes disclosed herein, that calcination must take place at a temperature of at least about 500° C. to about 700°, and preferably from about 600° to about 650°. Notwithstanding, it is important that the temperature of calcination not exceed about 700° C., and preferably no more than about 675° C. By maintaining the range of calcination within the range set forth herein, effective and useful adsorption properties are exhibited by the adsorbent blends produced by the processes disclosed herein. As evidence of the importance of calcination temperature, see FIG. 7, which utilized a 3A zeolite with a 50% potassium ion exchange (See Comparative Example 7).

The molecular sieve adsorbent blends exhibit a preferred pore structure. An analysis of this pore structure can be determined by mercury porismetry. Using data from analysis by mercury porismetry, the total particle porosity, medium pore diameter, volume of pores between 0.1 and 1.0 μm, and pore distribution coefficient can be determined.

It is preferable for the adsorbent blend to have a total particle porosity ranging from about 32% to about 40%.

It is also preferable that the median pore diameter is at least about 0.25 μm, more preferably greater than 0.4 μm and most preferably greater than 0.5 μm. The maximum median pore diameter is not critical but is practically about 1.5 μm.

It is also preferable that the pores are of an appropriate size, preferably pores that are between 0.1 and 1 μm. The distribution of pores can be determined by computation of "pore distribution coefficient." Pore distribution coefficient is defined herein by the following equation:

$$((A*B)+(C*D)+(E*F))*G \times 1000 = \text{Pore Distribution Coefficient}$$

Where:
A=Pores>1 μm (ml/g)
C=Pores<0.1 μm (ml/g)
E=Pores<1 μm and >0.1 μm (heart fraction) (ml/g)
G=Total Pore Volume (ml/g)
B=A/G
D=C/G
F=E/G Using pore distribution coefficient as defined above, it is preferable that the adsorbent blends have a pore distribution coefficient greater than 40 and preferably greater than 60. While higher pore distribution coefficients of over an 100 are not adverse, they may not be practical or necessary to produce efficient adsorbent products. A comparison of the performance of samples of adsorbents particles of the inventive composition versus conventional adsorbents is shown, for example, in Table 4. Note that comparative adsorbents had pore distribution coefficients less than 40, while those using inventive adsorbents were greater than 40 and generally greater than 60.

Figure 6:
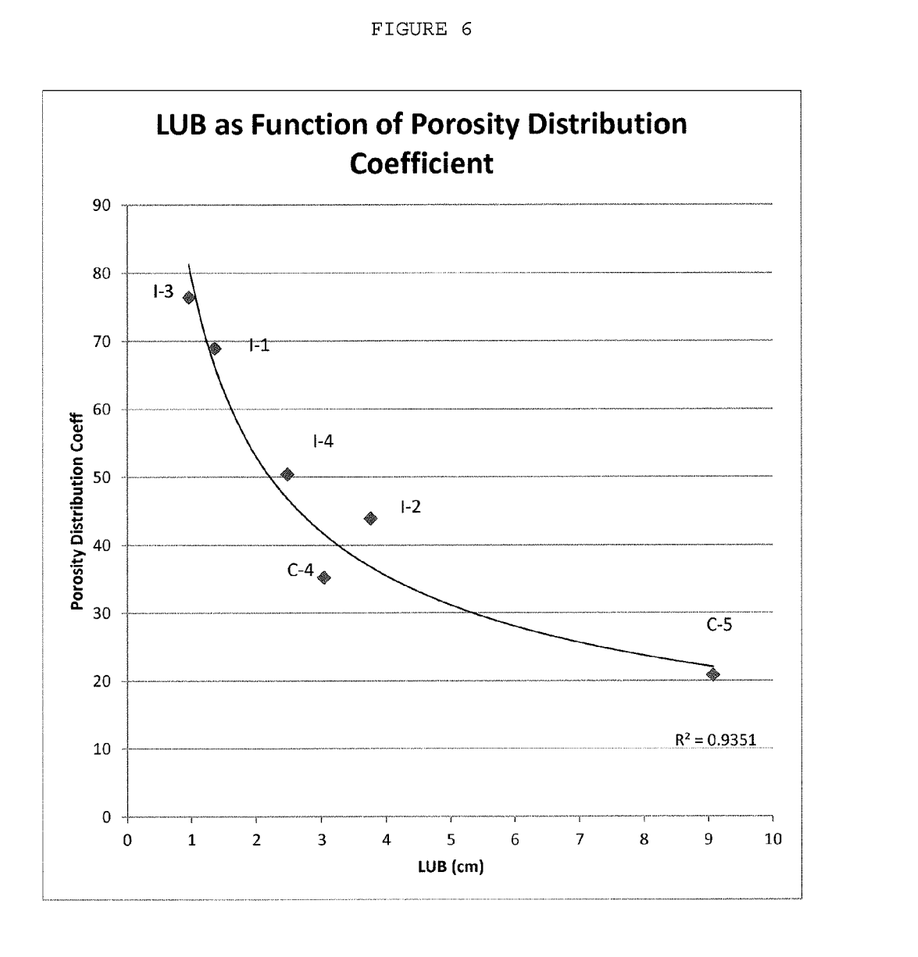
FIG. 6 compares the performance of various adsorbents from Example 1 based on the relationship between their pore distribution coefficient (PDC) and their length of unused bed (LUB).

In order to study the performance of various molecular sieve blends for removing water from a hydrocarbon feed stream, various criteria including breakthrough time, MTC, pore distribution coefficient length of unused bed (LUB) and selectivity are important criteria, as disclosed herein. Further, the relationship between pore distribution coefficient and LUB of various adsorbents is shown in FIG. 6.

Products produced by the disclosed processes show improved water adsorption rates. The adsorption rate can be determined using several different methods. For example, the water adsorption rate of the material can be determined by fitting a temperature profile data to a first order decay function represented by the expression $f = a \cdot e^{-kt}$. The slope of the curve, $-k$, represents the water adsorption rate for the material.

In another process to determine the adsorption rate of the molecular sieve adsorbent blends, the amount of the adsorbed product over a given period of time can be determined.

In a further process to determine the adsorption rate, the mass transfer zone of the blend can be compared to that of a conventional zeolite adsorption blend under given conditions. The shorter the mass transfer zone, the higher the adsorption rate.

Finally, the diffusion rate can be determined directly for certain gases or liquids. The higher the diffusion rate, the faster the adsorption rate.

It has been surprisingly discovered that by utilizing the disclosed adsorbents and processes for manufacture thereof, there is an improved water adsorption rate regardless of which method is used to measure that rate. This improvement in adsorption rate is at least about 10 percent and as high as 350 percent, compared to products containing conventional attapulgite clay binders.

It has also been surprisingly discovered that even when reduced quantities of a hydrophobic silicon based binder are utilized in adsorbents, in comparison to prior art adsorbent products using conventional clay binders, the rate of adsorption increases. This improvement is at least 10 percent and in many cases as much as 30 percent or more. This improvement is especially apparent when a granulation seed process, preferably using a clay binder in the seed, is utilized for the production of the adsorbent products.

It has also been surprisingly discovered that the disclosed adsorbents produced by the disclosed processes exhibit improved crush strength and hysteresis values superior to adsorbents prepared using conventional clay binding agents.

An additional surprising discovery is that by using a hydrophobic silicon based material as a binder material, there is a significant reduction in the production of undesirable oligomers and polymers when the zeolite/hydrophobic silicon based adsorbent blends are utilized as a dehydration agent. In addition, because of the reduction of the production of these oligomers and polymers, the life expectancy of the zeolite blend is also increased.

These improvements are especially apparent when the adsorbents are formed using seeds, formed by a granulation seed process, preferably utilizing a clay binder.

Further, using the adsorbents disclosed herein, there is less of a need for regeneration and lower regeneration temperatures resulting in additional cost savings.

In addition, there is an improvement in selectivity of the material that is desired to be adsorbed.

These improvements are shown by the following examples. In these examples the sample materials are tested in the form as used for a molecular sieve blend.

EXAMPLES

Example 1

To compare the performance of various adsorbents and to show the surprising selectivity of a zeolite blend comprising a hydrophilic zeolite and a hydrophobic silicon based binder, and in some embodiments a seed utilizing a clay binder, samples of various adsorbents with different compositions are prepared or obtained. These compositions are compared to illustrate their selectivity for the removal of water from an ethanol stream using a process.

The selected adsorbent sample is dried overnight at 240° C. The sample is cooled in a desiccator to room temperature. 20 grams of the sample is placed in a 2 neck 50 ml round bottom flask. A thermocouple is inserted into the flask via a thermocouple injection port. The flask is capped and placed in a water bath maintained at 30° C. The sample is then allowed to equilibrate for 15 minutes to achieve temperature equilibrium. Using a glass syringe, 25 ml of a test solution (90/10 mixture of ethanol/water) is drawn from a master container, which also has been equilibrated in temperature to 30° C. The test solution is then injected into the flask and the resulting temperature profile is collected over 120 seconds. The maximum temperature rise exhibited from each material during this period is then used to calculate the selectivity of the material ($\alpha$) by utilizing the following expression:

$$\alpha = T\text{max} - T\text{initial}$$

Figure 1:
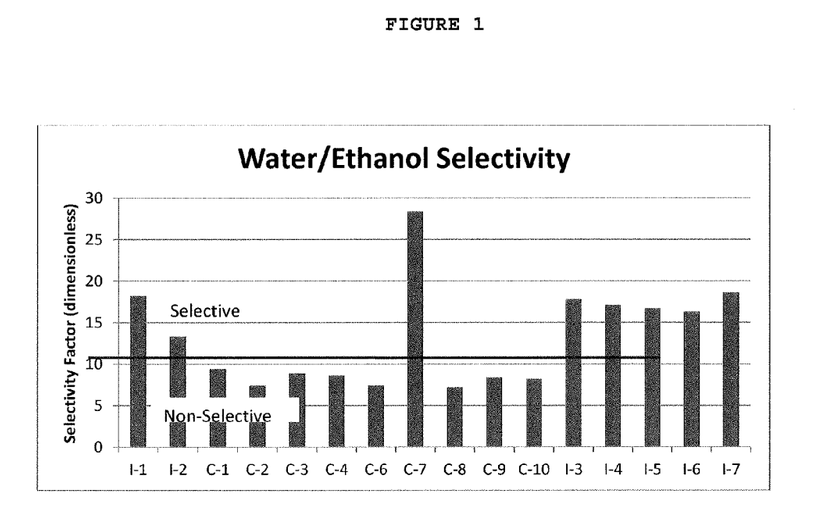
FIG. 1 lists the maximum increase in temperature during the test process for various sample products described in Example 1.

The basic premise of this testing procedure is that the more selective a material is for water, the higher the temperature rise during an adsorption process. It is believed that a material that exhibits low selectivity shows a lower temperature rise due to larger amounts of ethanol co-adsorption which blocks active zeolite sites. The data from the tests of various samples is collected and is shown in various Tables and Figures. Table 1 and FIG. 1 show the maximum increase in temperature during the test process. The maximum increase in temperature may be exhibited by the samples at various times throughout the test process.

Pursuant to this test, a "strong" separation factor is a value of 30° C. with no separation at 0° C. The defined threshold for a "non-selective material" is less than 10° C. The determination of a threshold of 10° C. for a "non-selective material" was determined after observation of materials known for their selectivity or lack of selectivity when analyzed alone. For example, for materials that are hydrophobic, such as a high silica ZSM-5 and pure silica (such as colloidal silica HS-30 from WR Grace), poor selectivity results are obtained. In addition, a number of hydrophilic materials are tested, the compositions of which are described below. Not surprisingly, pure zeolite 3A, a known hydrophilic material, has a high water selectivity. In addition, Actigel® 208, which is comprised of an attapulgite material, has a high selectivity factor of about 18° C. Other samples which exhibit a selectivity factor above 10° C. are a blend of 10% colloidal silica (HS-30 from WR Grace) with 90% zeolite 3A (from Zeochem) (referenced as I-1), a blend of an organo siloxane emulsion (IE-2404 supplied by Dow Corning) with zeolite 3A (from Zeochem), wherein the quantity of the siloxane material is about 5% of the blend and the quantity of the zeolite 3A is about 95% of the blend (referred to as I-2), and samples containing zeolite 3A, various quantities of the siloxane emulsions (IE-2404), and various volumes of seeds formed by a granulation process, wherein the seeds contain zeolite and various quantities of various clay binders (referred to as I3-I8). The tested materials are described below and a comparison of their selectivity is shown in Table 1 and FIG. 1. (For purposes of this disclosure, a material is "selective" for the adsorption of water in a water/ethanol mix when tested using the described process if the increase in temperature is greater than 10° C. A material is "non-selective" if the increase is less than 10° C.)

Sample Descriptions:
Inventive Sample 1 (I-1)
This material is 10% colloidal silica (HS-30 from WR Grace) and 90% 3A Zeolite powder from Zeochem. The material is in the form of spheres.
Inventive Sample 2 (I-2)
This material is a blend of a siloxane based binder from Dow Corning containing dimethyl siloxane, methyl silsesquioxanes and n-octyl silsequioxanes (IE 2404) with zeolite 3A powder (Zeochem), where the quantity of the siloxane based binder is about 5% and the quantity of the zeolite 3A powder is about 95%.
Comparative Sample 1 (C-1):
This material is a 10% binder with 90% 3A zeolite powder from Zeochem, wherein the binder is a 50/50 blend of colloidal silica (HS-30) and Actigel® 208 clay (from Active Minerals). The material is in the form of spheres.
Comparative Sample 2 (C-2):
The material is comprised of 10% Actigel® 208 attapulgite clay from Active Minerals and 90% 3A Zeolite powder from Zeochem. The material is in the form of spheres.
Comparative Sample 3 (C-3):
Manufactured by Ceca (Arkema is parent company). The material is comprised of 20% attapulgite clay and 80% 3A zeolite powder. The material is in the form of spheres.
Comparative Sample 4 (C-4):

Manufacture by Zeochem. The material is comprised of 20% attapulgite clay (from Active Minerals) and 80% 3A zeolite powder. The material is in the form of spheres.
Comparative Sample 5 (C-5):
Manufactured by WR Grace. The material is comprised of 20% attapulgite clay and 80% 3A zeolite powder. The material is in the form of spheres.
Comparative Sample 6 (C-6):
Manufactured by Hengye. The material is comprised of 20% attapulgite clay and 80% 3A zeolite powder. The material is in the form of spheres.
Comparative Sample 7 (C-7):
Manufactured by Zeochem. This is a Zeolite 3A powder.
Comparative Sample 8 (C-8):
Manufactured by WR Grace. This is a colloidal silica solution with a 30% $SiO_2$ content. Before testing the colloidal silica material is dried at 80° for about 1 hour, 110° C. for about 1 hour, 250° C. for 1 hour, and 550° C. for about 1 hour to produce a $SiO_2$ powder.
Comparative Sample 9 (C-9):
Manufactured by Zeochem. This is a high Si/Al ratio (600) ZSM-5 zeolite powder. This material is in an extruded form.
Comparative Sample 10 (C-10):
Actigel® 208 (manufactured by Active Minerals). This is an attapulgite clay powder.
Comparative Sample 11 (C-11):
Manufactured by UOP. The sample contains 20% clay and 80% 3A zeolite powder. The sample is in the form of extrusions.
Comparative Sample 12 (C-12):
Minugel® MB (manufactured by Active Minerals). This is an attapulgite clay powder.
Inventive Sample 3 (I-3)
This sample is 5% siloxane based product (IE-2404 from Dow Corning), 95% 3A zeolite powder from Zeochem (quantities determined without consideration of quantity of the seed) and a seed, wherein the seed comprises 15% of the total adsorbent, by volume. The seed is 90% 3A zeolite powder from Zeochem and 10% Actigel® 208 from Active Minerals.
Inventive Sample 4 (I-4)
This sample is 5% siloxane based product (IE-2404 from Dow Corning), 95% 3A zeolite powder from Zeochem (quantities determined without consideration of quantity of the seed) and a seed, wherein the seed comprises 30% of the adsorbent by volume. The seed is 90% 3A zeolite powder from Zeochem and 10% Actigel® 208 from Active Minerals.
Inventive Sample 5 (I-5)
This sample is 5% siloxane based product (IE-2404 from Dow Corning), 95% 3A zeolite powder from Zeochem (quantities determined without consideration of quantity of the seed) and a seed, wherein the seed comprises 15% of the adsorbent by volume. The seed is 80% 3A zeolite powder from Zeochem and 20% Minugel MB from Active Minerals.
Inventive Sample 6 (I-6)
This sample is 5% siloxane based product (IE-2404 from Dow Corning), 95% 3A zeolite powder from Zeochem (quantities determined without consideration of quantity of the seed) and a seed, wherein the seed comprises 15% of the adsorbent by volume. The seed is 90% 3A zeolite powder from Zeochem and 10% halloysite from Active Minerals.
Inventive Sample 7 (I-7)
This sample is 5% siloxane based product (IE-2404 from Dow Corning), 95% 3A zeolite powder from Zeochem (quantities determined without consideration of quantity of the seed) and a seed wherein the seed comprises 15% of the adsorbent by volume. The seed is 90% 3A zeolite powder from Zeochem and 10% sepiolite from Tolsa (Pansil-400).
Inventive Sample 8 (I-8)
This sample is 10% siloxane based product (IE-2404 from Dow Corning), 90% 3A zeolite powder from Zeochem (quantities determined without consideration of quantity of the seed) and a seed wherein the seed comprises 15% of the adsorbent by volume. The seed is 90% 3A zeolite powder from Zeochem and 10% Actigel® 208 from Active Minerals.

TABLE 1

| Water/Ethanol Selectivity (See also FIG. 1) | |
|---|---|
| Sample | ° C. |
| I-1 | 18.2 |
| I-2 | 13.3 |
| C-1 | 9.4 |
| C-2 | 7.4 |
| C-3 | 8.9 |
| C-4 | 8.6 |
| C-6 | 7.4 |
| C-7 | 28.4 |
| C-8 | 7.2 |
| C-9 | 8.4 |
| C-10 | 8.2 |
| I-3 (Actigel ® 15% seed) | 17.8 |
| I-4 (Actigel ® 30% seed) | 17.1 |
| I-5 (Minugel seed) | 16.7 |
| I-6 (Halloysite seed) | 16.3 |
| I-7 (Sepiolite seed) | 18.6 |

It is clear from Table 1 and FIG. 1 that even though pure colloidal silica has a very low water selectivity individually, because it is hydrophobic, when combined with a zeolite 3A powder to form I-1, the combined materials have a high selectivity factor for water in a water: ethanol mixture, almost as high as that of a conventional clay binder used alone, which is hydrophilic. It is also clear that a blend of a siloxane based binder (IE 2404) with zeolite 3A (I-2) also produces an adsorbent blend having a high selectivity factor. It is also clear that the utilization of a granulation formed seed, which seed is formed using a clay binder, during the production of an adsorbent blend otherwise containing a colloidal silica and a 3A zeolite also produces adsorbent blends having a high selectivity factor. None of the other blends of materials showed selectivity within the range of the combination of hydrophilic zeolite 3A and the hydrophobic silicon based binder, the siloxane based binder or the adsorbent blends containing a seed, including several combinations of hydrophilic 3A zeolite with conventional attapulgite clay binders.

Example 2

To compare the performance of various materials for the production of undesired hydrocarbons, which are commonly produced during some adsorption processes, which hydrocarbons are generically referred to as "coke", a coking test is run with various samples. The tests illustrated the effectiveness of the use of a blend of a hydrophobic silicon based binder with a hydrophilic zeolite or an adsorbent blend containing a hydrophobic silicon based binder and a hydrophobic zeolite, which blend utilized a seed, formed using a zeolite and a clay binder, over other samples to reduce the production of coke during a standard coking test.

0.1 grams of each sample is weighed and dried overnight and is then placed in a desiccator. The sample is exposed for 12 hours at 450° C. to a gas stream comprising 4% by volume of a reactive diene (1,3-butadiene) with the balance of the gas stream comprising nitrogen at a gas flow rate of 60 ml/min. The sample is monitored for its tendency to form green oil resulting in a carbon deposition, which is referenced as coke.

The samples tested are selected from samples from Example 1. The results are shown in Table 2 and FIG. 2.

TABLE 2

Coking Results

| Sample | Coking Results (mmol/g/min) |
|---|---|
| C-7 | 2.74E−10 |
| I-3 | 5.83E−09 |
| I-4 | 9.26E−09 |
| I-5 | 6.52E−09 |
| I-6 | 6.52E−09 |
| I-7 | 3.77E−09 |
| I-1 | 2.40E−09 |
| I-2 | 1.03E−09 |
| C-4 | 2.47E−08 |
| C-5 | 1.23E−08 |
| C-11 | 1.27E−08 |

Figure 2:
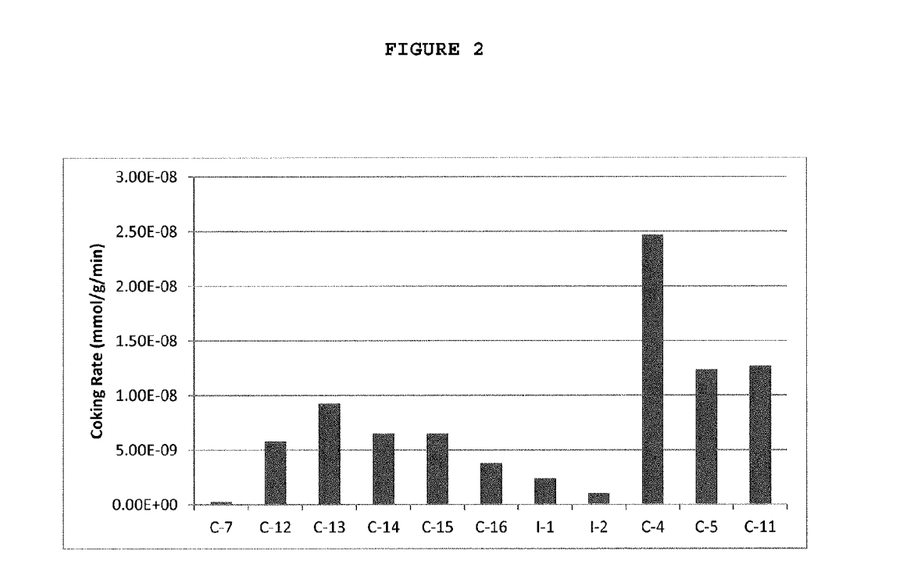
FIG. 2 compares the reactivity of various sample products from Example 2 for the production of 1,3 butadiene.

As is clear from the results shown in Table 2 and FIG. 2, a composition comprising a hydrophobic colloidal silica binder or a siloxane binder mixed with a hydrophilic zeolite 3A or an adsorbent blend containing a hydrophobic silicon based binder and a hydrophobic zeolite, containing a seed, which seed is formed using a zeolite and a clay binder, performed better than any of the comparative clay binder examples by producing less total coke during the test procedure. It is also clear that the utilization of a seed consisting of a hydrophilic 3A zeolite and a conventional clay binder in the production of the molecular sieve blend has no adverse effect on the butadiene reactivity of the adsorbent blend.

Example 3

To compare the water adsorption rates of various materials, an adsorption test is run comparing the water adsorption kinetics of materials determined by fitting a temperature profile data to a first order decay function, as described previously. The products chosen are selected from the group of samples used in Example 1.

The sample to be tested is dried overnight at 240° C. The sample is cooled in a desiccator to room temperature. 20 grams of the sample is placed in a 2 neck 50 ml round bottom flask. A thermocouple is inserted into the flask via a thermocouple injection port. The flask is capped and is placed into a water bath maintained at 30° C. The sample is then allowed to equilibrate for 15 minutes to achieve temperature equilibrium. Using a glass syringe, 25 ml of a test solution (90/10 mixture of ethanol/water) is drawn from the master container, which also has been equilibrated in temperature to 30° C. The test solution is then injected into the flask and the resulting temperature profile is collected. The data is then analyzed by fitting a first order decay model to the resultant profile as discussed above. The slope from that decay is representative of the apparent water mass transfer. The results are shown in FIG. 3.

Figure 3:
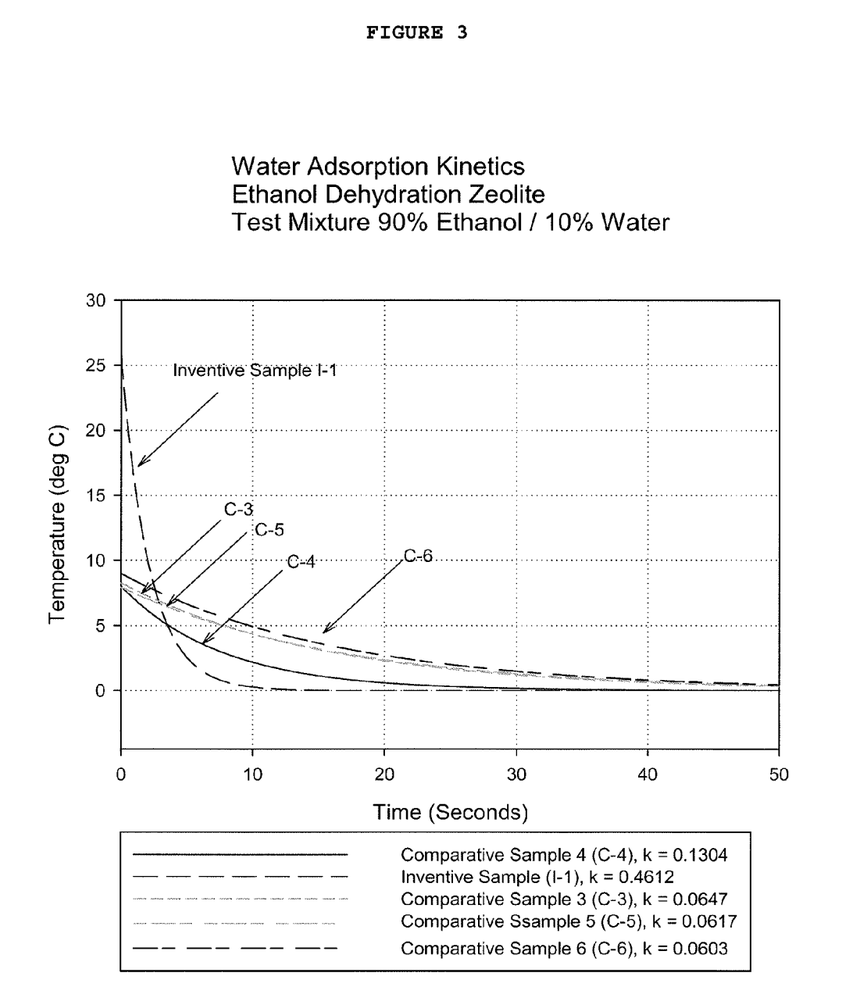
FIG. 3 compares the water adsorption kinetics of various sample products from Example 3.

As is clear from the tests shown in FIG. 3, the most favorable water adsorption kinetics disclosed is by I-1. The high degree of heat evolution and steepness of the thermal front for this sample indicates very favorable and fast water adsorption in the presence of ethanol. This uptake is surprisingly 3-4 times higher than the best prior art adsorbent, indicating superior water uptake properties.

Example 4

To classify a material as "hydrophobic" or "hydrophilic", a test was developed. The test comprised taking approximately 10 grams of a test sample and drying it for about four (4) hours at 230° C. The material to be tested is in the form of particles. As beads, they pass through a 4 mm×4 mm mesh. As extrusions, they have a ⅛" diameter (3.1 mm). The sample materials are tested in the form as used for the molecular sieve blend. The dried sample is then weighed and placed in a flow of air and hydrated to a relative humidity of 80% at 1 atm and 20° C. The resulting weight gain from water adsorption is then recorded and plotted to determine the maximum water capacity, as well as the relative water adsorption rate.

The samples are evaluated for total water adsorption capacity as well as relative adsorption rate. To measure the ultimate adsorption capacity, the final weight gain after 7.5 hours is determined. A relative rate of water adsorption of the materials is also calculated after 60 minutes. A sample is considered "hydrophobic" if it has an adsorption capacity of less than 5.5% (wt.) after 7.5 hours and a relative rate of adsorption of less than 0.05% (wt.) per minute after 60 minutes. From that analysis, the zeolite sample (C-7) as well as the clay binders used alone (C-10 and C-12) exhibit adsorption characteristics consistent with "hydrophilic" materials, whereas the silica binder (C-8) shows "hydrophobic" characteristics.

Figure 4:
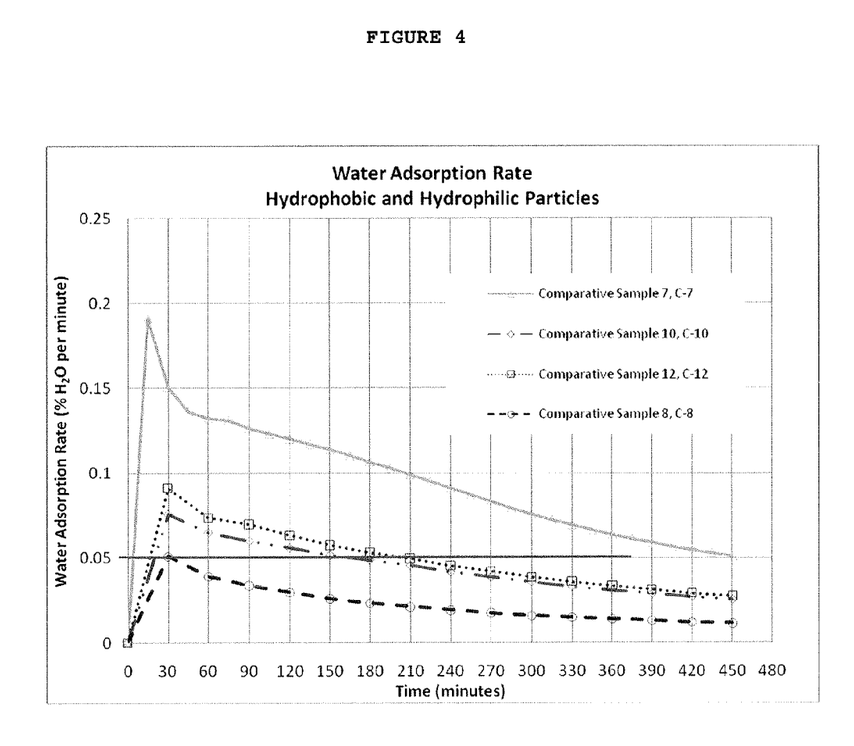
FIG. 4 compares the water adsorption rate for various samples from Example 4.
Figure 5:
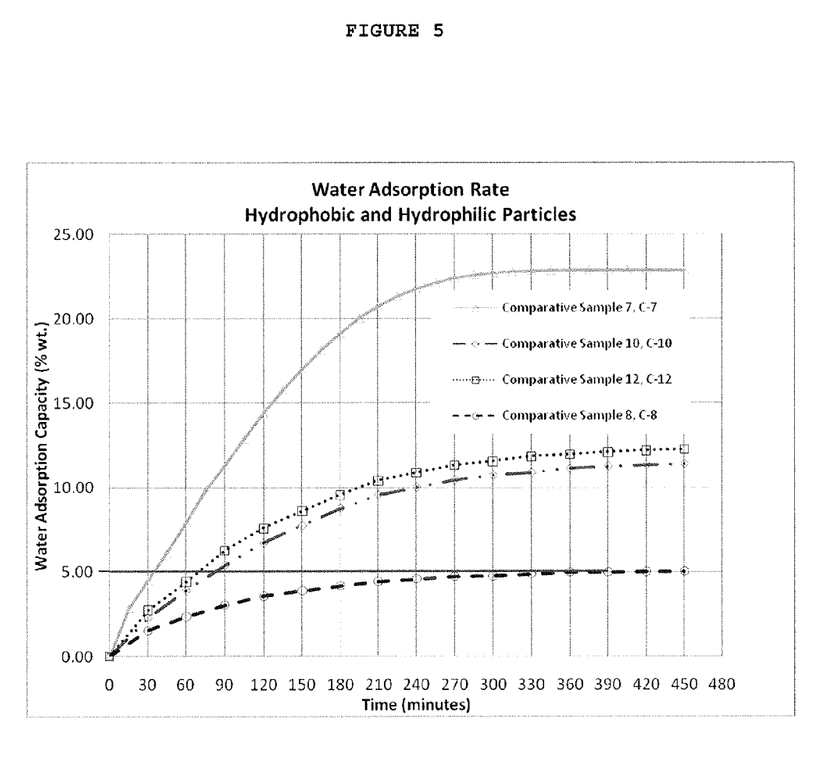
FIG. 5 compares the water adsorption capacity for various products from Example 4.

The results of these tests are shown in Table 3 and FIGS. 4 and 5:

TABLE 3

| | Ultimate H2O Capacity % (wt.) @ $t_{450}$ | H2O Adsorption Rate % (wt.) per min @ $t_{60}$ |
|---|---|---|
| C-7 | 22.89 | 0.130 |
| C-10 | 11.50 | 0.0652 |
| C-8 | 5.03 | 0.0393 |
| C-12 | 12.35 | 0.0737 |

Example 5

To compare the impact of the binder system on the pore structure of adsorbents, mercury porisemtry data was collected and analyzed for various adsorbents and is shown in Table 4. A standard mercury intrusion experiment is performed utilizing a Micromeritics Autopore IV 9500. The data is analyzed for the adsorbent's total porosity, median pore size, and pore distribution coefficient, which phrase is defined as follows:

$((A*B)+(C*D)+(E*F))*G \times 1000=$Pore Distribution Coefficient

Where:
A=Pores>1 μm (ml/g)
C=Pores<0.1 μm (ml/g)
E=Pores<1 μm and >0.1 μm (heart fraction) (ml/g)
G=Total Pore Volume (ml/g)
B=A/G
D=C/G
F=E/G

TABLE 4

| Sample | Total Porosity (%) | Median Pore Diameter—MPD (μm) | PDC |
|---|---|---|---|
| I-1 | 37.9 | 0.47 | 68.9 |
| I-2 | 34.7 | 0.72 | 43.9 |
| I-3 | 39.0 | 0.59 | 76.4 |
| I-4 | 34.4 | 1.01 | 50.4 |
| I-5 | 36.8 | 0.70 | 81.2 |
| I-6 | 37.0 | 0.59 | 75.2 |
| I-7 | 36.7 | 0.75 | 80.3 |
| I-8 | 38.3 | 0.79 | 92.8 |
| C-4 | 34.0 | 0.08 | 35.2 |
| C-5 | 30.5 | 0.16 | 20.8 |

Example 6

In order to study the performance of adsorbents for removing water from hydrocarbon streams, a dynamic water adsorption test is performed on various samples, as shown in Table 5. The tests consist of packing a 2 inch adsorption column to a height of approximately 19 cm with the adsorbent to be studied. A carrier gas is then passed through the adsorbent column containing about 2100 ppmV $H_2O$ vapor at 25° C. and about 50 psi. The resulting breakthrough curve is collected and analyzed.

TABLE 5

| Sample | Breakthrough Time (min) | Length of unused Bed—LUB (cm) |
|---|---|---|
| I-1 | 524 | 1.36 |
| I-2 | 445 | 2.76 |
| I-3 | 527 | 0.96 |
| I-4 | 463 | 2.48 |
| I-5 | 496 | 2.23 |
| I-6 | 488 | 2.29 |
| I-7 | 494 | 2.12 |
| I-8 | 461 | 1.64 |
| C-4 | 465 | 3.04 |
| C-5 | 287 | 9.07 |

From this dynamic evaluation, one can extract useful adsorption equilibria and dynamic information. One such useful dynamic criteria is Length of the Unused Bed, or LUB. LUB is defined as half the spread of the mass transfer zone. Quantifying the length describes the shape of the breakthrough front as it travels through the packed adsorbent column.

To calculate, a feed mixture (in this case water and air) is introduced into a packed adsorbent column. As the bed is continuously fed with the feed, the bed becomes saturated with the adsorbate (in this case, the water). The concentration for the portion of the bed at saturation is known as the equilibrium zone, and corresponds to the adsorbent loading capacity for that adsorbate at the feed conditions. The part of the bed where the feed is still equal to the feed concentration is known as the LUB. Between the two exists an intermediate zone, where there is a transfer from a fluid phase to an adsorbed phase, which is known as the mass transfer zone. When the leading edge of the mass transfer zone reaches the outlet, the bed is said to "breakthrough".

If one plots the concentration of the water in the bed effluent as a function of time, a curve is developed. From this curve, the LUB can be calculated by the following equation:

$$LUB = L\frac{(tm - tb)}{tm}$$

LUB=Length of unused Bed
L=length (height) of packed bed
$t_m$=midpoint time, time at which $$Xeffluent = \frac{Xfeed}{2}$$

tb=breakthrough time, time at which Xeffluent=$X_b$
X=concentration of water in the feed Adsorbents with higher porosity distribution coefficient and lower LUB are more effective as adsorbents. A comparison of porosity distribution coefficient versus LUB for various adsorbents from the Examples is shown in FIG. 6.

Example 7

In order to study the impact of calcination temperature on the adsorption of a molecular sieve, an adsorption of water and methanol test is run with zeolite 3A from comparative sample C-7 with 50% potassium ion exchange, which is calcined at various temperatures. The zeolite 3A sample is dried using a temperature ramp of 35° C. per hour to 250° C. and then held at 250° C. overnight. The sample is then sealed. Aliquots of this sample are calcined one at a time at differing temperatures for 90 minutes per temperature. The temperatures used to calcine the samples are 300° C., 400° C., 500° C., 600° C., 650° C., 700° C., and 750° C. After each of the 90 minute calcinations, the sample is cooled to a safe handling temperature in a desiccator.

Figure 7:
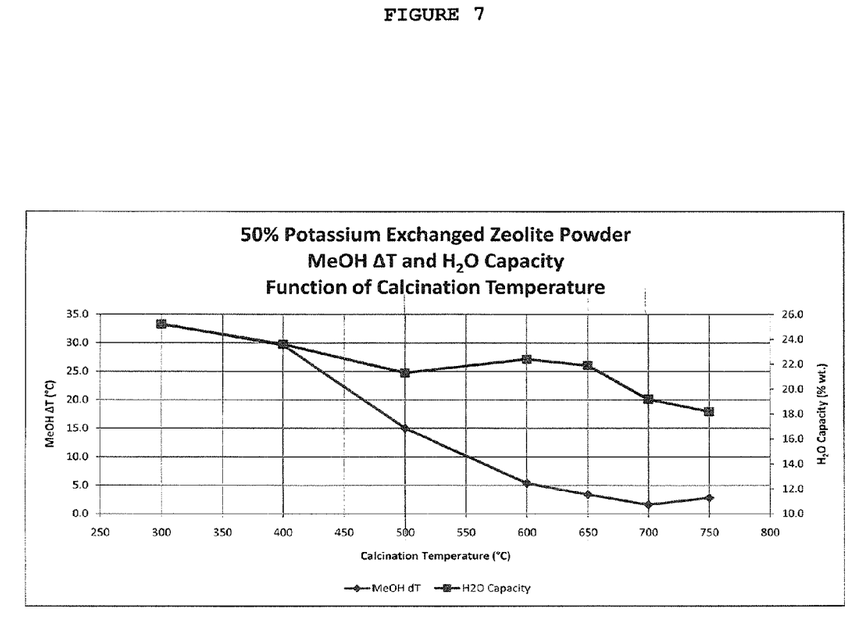
FIG. 7 compares co-adsorption percentages of methanol and water of a zeolite 3A of Comparative Example calcined at various calcination temperatures, wherein the potassium ion exchange of the zeolite 3A is 50%.

Each sample is analyzed for its temperature rise when 10 g of the sample is exposed to 25 mL of methanol at 30 C. Each sample is also analyzed for its equilibrium water capacity at 50% relative humidity. The results of these tests are shown in FIG. 7.

As is clear, the samples exhibiting acceptable adsorption of methanol of 20% or less had been calcined at temperatures from 500° C. to 750° C. More acceptable water adsorption is exhibited with calcination temperatures between 650° C. to 750° C.

Although the invention has been described in detail, it is clearly understood that the disclosure is not to be taken as any limitation on the invention.

The invention claimed is:

1. A molecular sieve blend for dehydration of a gaseous or liquid hydrocarbon feed stream comprising
    a hydrophilic low silica zeolite with a ratio of $SiO_2$ to $Al_2O_3$ of less than 5;
    a hydrophobic silicon containing binder; and
    a seed, blended with the hydrophilic low silica zeolite and the silicon containing binder to form the molecular sieve blend, wherein the seed comprises the hydrophilic low silica zeolite and a clay binder; and
    wherein the amount of the clay binder present in the molecular sieve blend comprises from about 0.5% to about 5% of the blend by weight.

2. The molecular sieve blend of claim 1 wherein the hydrophilic low silica zeolite comprises zeolite A.

3. The molecular sieve blend of claim 1 wherein the hydrophilic low silica zeolite comprises zeolite 3A.

4. The molecular sieve blend of claim 1, wherein the hydrophobic silicon containing binder comprises from about 2% to 30%, by weight, of the molecular sieve blend.

5. The molecular sieve blend of claim 1, wherein the hydrophobic silicon containing binder comprises from about 2% to 10%, by weight, of the molecular sieve blend.

6. The molecular sieve blend of claim 1, wherein the hydrophobic silicon containing binder comprises colloidal silica.

7. The molecular sieve blend of claim 1, wherein the hydrophobic silicon containing binder comprises a siloxane based material.

8. The molecular sieve blend of claim 1, wherein the hydrophilic low silica zeolite is ion exchanged with potassium ions to at least 30%.

9. The molecular sieve blend of claim 1, wherein the hydrophilic low silica zeolite is ion exchanged with potassium ions in a range from about 45% to about 65%.

10. The molecular sieve blend of claim 1, wherein it has a median pore diameter of at least 0.25 μm and less than about 1.5 μm.

11. The molecular sieve blend of claim 1, wherein it has a median pore diameter greater than 0.40 μm.

12. The molecular sieve blend of claim 1, wherein it has a total particle porosity from about 32% to about 40%.

13. The molecular sieve blend of claim 1, wherein it has a pore distribution coefficient of at least about 40.

14. The molecular sieve blend of claim 1, wherein it has a pore distribution coefficient of at least about 60.

15. The molecular sieve blend of claim 1, wherein the clay binder comprises from about 0.5 to about 3% by weight of the molecular sieve blend.

16. The molecular sieve blend of claim 1, wherein the clay binder comprises from about 5 to about 20%, by weight, of the seed.

17. The molecular sieve blend of claim 1, wherein a ratio of the clay binder to the hydrophilic low silica zeolite in the seed is from about 1:4 to 1:20.

18. The molecular sieve blend of claim 1, wherein the seed comprises from about 0.5 to about 25% by volume of the molecular sieve blend.

19. A molecular sieve blend for dehydration of a gaseous or liquid hydrocarbon feed stream comprising
a hydrophilic zeolite A;
a hydrophobic colloidal silica binder; and
a seed, blended with the zeolite A and the colloidal silica binder to form the molecular sieve blend;
wherein the seed comprises the hydrophilic zeolite A and a clay binder;
wherein the amount of clay binder present in the molecular sieve blend comprises from about 0.5% to about 5%, by weight; and
wherein the hydrophilic zeolite A is ion exchanged with potassium ions in a range from about 45% to about 65%.

20. A molecular sieve blend for dehydration of a gaseous or liquid hydrocarbon feed stream comprising
a hydrophilic zeolite 3A;
a hydrophobic colloidal silica binder; and
a seed, blended with the zeolite 3A and the colloidal silica binder to form the molecular sieve blend;
wherein the seed comprises the hydrophilic zeolite 3A and a clay binder;
wherein the hydrophilic zeolite 3A is ion exchanged with potassium ions in a range from 45% to about 65%;
wherein the colloidal silica binder comprises about 2% to about 10%, by weight, of the molecular sieve blend; and
wherein the molecular sieve blend has a pore distribution coefficient of at least about 40.

* * * * *